United States Patent
Dorronsoro Diaz et al.

(10) Patent No.: US 10,213,358 B2
(45) Date of Patent: Feb. 26, 2019

(54) MINIATURISED INSTRUMENT FOR SIMULATING SIMULTANEOUS VISION BY GENERATING MASKS

(71) Applicant: CONSEJO SUPERIOR DE INVESTIGACIONES CIENTIFICAS (CSIC), Madrid (ES)

(72) Inventors: Carlos Dorronsoro Diaz, Madrid (ES); Susana Marcos Celestino, Madrid (ES)

(73) Assignee: CONSEJO SUPERIOR DE INVESTIGACIONES CIENTIFICAS (CSIC), Madrid (ES)

(*) Notice: Subject to any disclaimer, the term of this patent is extended or adjusted under 35 U.S.C. 154(b) by 0 days.

(21) Appl. No.: 15/763,986

(22) PCT Filed: Sep. 27, 2016

(86) PCT No.: PCT/ES2016/070673
§ 371 (c)(1),
(2) Date: Mar. 28, 2018

(87) PCT Pub. No.: WO2017/055656
PCT Pub. Date: Apr. 6, 2017

(65) Prior Publication Data
US 2018/0271741 A1    Sep. 27, 2018

(30) Foreign Application Priority Data
Sep. 30, 2015 (ES) .................. 201531397

(51) Int. Cl.
*A61H 5/00* (2006.01)
*A61B 3/02* (2006.01)
(Continued)

(52) U.S. Cl.
CPC ............ *A61H 5/005* (2013.01); *A61B 3/02* (2013.01); *A61B 3/0285* (2013.01); *A61F 2/16* (2013.01); *A61H 2201/10* (2013.01)

(58) Field of Classification Search
CPC ....... A61B 3/032; A61B 3/024; A61B 3/0033; A61B 3/08
(Continued)

(56) References Cited

U.S. PATENT DOCUMENTS

| | | | |
|---|---|---|---|
| 2011/0080562 A1 | 4/2011 | Iizuka et al. | |
| 2012/0075585 A1* | 3/2012 | Dorronsoro Diaz | A61B 3/08 351/222 |
| 2012/0154742 A1* | 6/2012 | Fernandez Martinez | A61B 3/0025 351/201 |

FOREIGN PATENT DOCUMENTS

| | | |
|---|---|---|
| EP | 2631891 A1 | 8/2013 |
| ES | 2346175 A1 | 10/2010 |
| ES | 2535126 A1 | 5/2015 |
| JP | 2011250981 A | 12/2011 |
| JP | 2012068551 A | 4/2012 |

OTHER PUBLICATIONS

Radhakrishnan et al., "Adaption to optically induced simultaneous bifocal vision", Investigative Ophthalmology & Visual Science, ARVO Annual Meeting, Abstract, Jun. 2015, vol. 56, 2905, 2 pages.
(Continued)

*Primary Examiner* — Mohammed A Hasan
(74) *Attorney, Agent, or Firm* — Hayes Soloway PC

(57) ABSTRACT

A miniaturised instrument for simulating simultaneous vision by generating masks is provided with a single image-forming optical channel. The instrument comprises: a mask-generating element (EGM) which generates at least two complementary masks, with a temporal frequency of alternation such that when one partially blocks the incident light,
(Continued)

the other allows the incident light to partially pass, and vice-versa; an adjustable lens (LA) of variable optical power which generates, with said frequency of alternation, at least two different optical powers corresponding to at least two observation distances. The EGM and the LA are located in a single optical channel via which the incident light circulates, such that each mask of the EGM is temporally synchronised with a power of the LA. The combination of all the masks and optical powers produces, via high-speed temporal fusion, a pupil pattern wherein at least two optical powers corresponding to at least two observation distances are combined.

20 Claims, 8 Drawing Sheets

(51) Int. Cl.
*A61B 3/028* (2006.01)
*A61F 2/16* (2006.01)
(58) Field of Classification Search
USPC .......................................... 351/203
See application file for complete search history.

(56) References Cited

OTHER PUBLICATIONS

Pablo de Gracia et al., "Experimental Simulation of Simultaneous Vision", The Association for Research in Vision and Ophthalmology, Inc., Investigative Ophthalmology & Visual Science, 2013, vol. 54, No. 1, 415-422, 8 pages.
VInase et al., "Testing vision with angular and radial multifocal designs using Adaptive Optics", Elsevier, Institute of Optics, Spanish National Research Council (CSIC), Serrano, 121, Madrid 28006, Spain, Vision Research, vol. 132, 2017, pp. 85-96.
Dorronsoro Diaz et al., "Visual Performance and perception with bifocal and trifocal presbyopia corrections simulated using a hand-held simultaneous vision device", ARVO Annual Meeting Abstract, Jun. 2015, Investigative Ophthalmology & Visual Science Jun. 2015, vol. 56, No. 4306, 2 pages.
Dorronsoro Diaz et al., "Visual testing of segmented bifocal corrections with a compact simultaneous vision simulator", ARVO Annual Meeting Abstract, Apr. 2014, Investigative Ophthalmology & Visual Science Apr. 2014, vol. 55, No. 781, 2 pages.

* cited by examiner

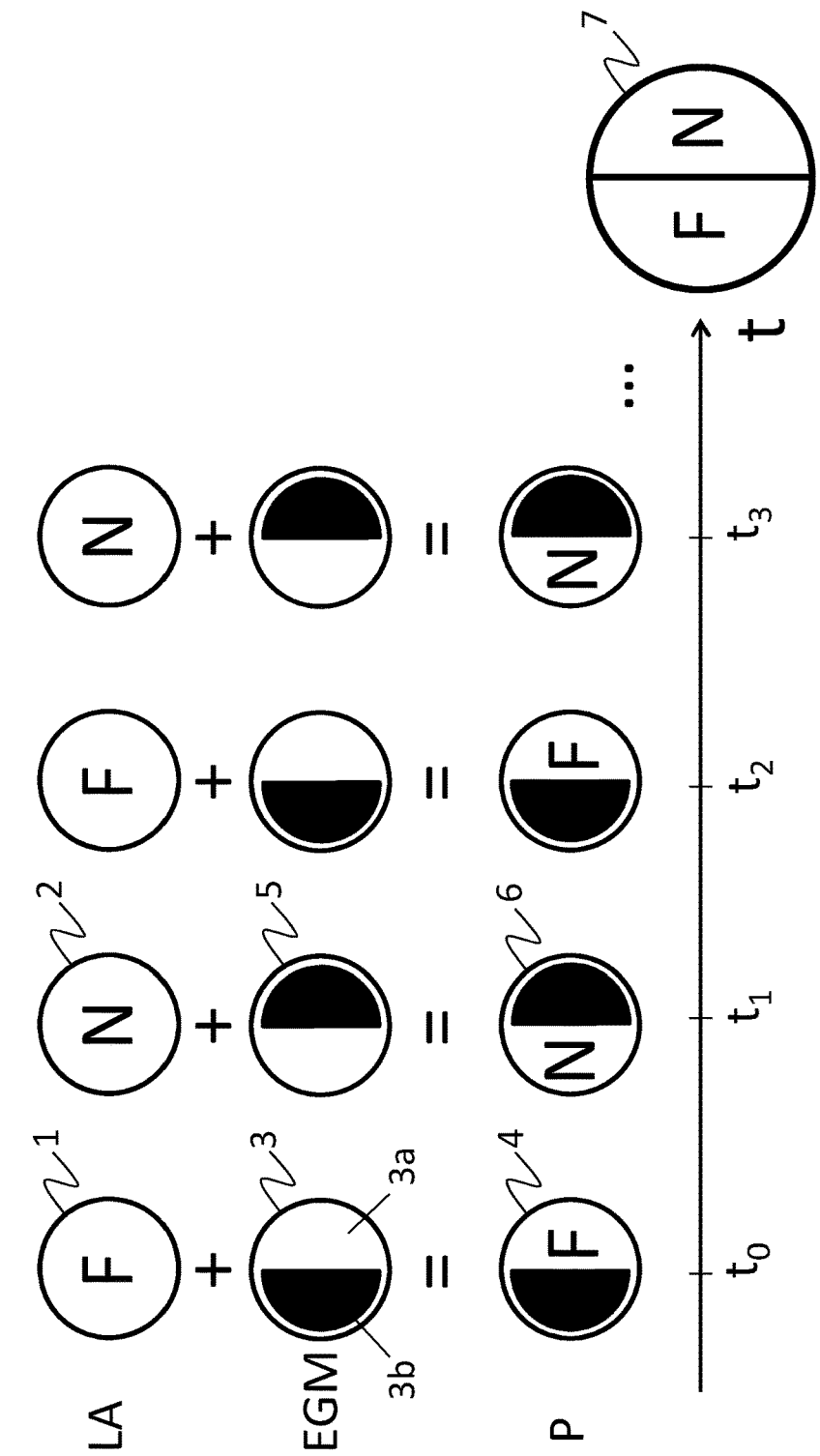

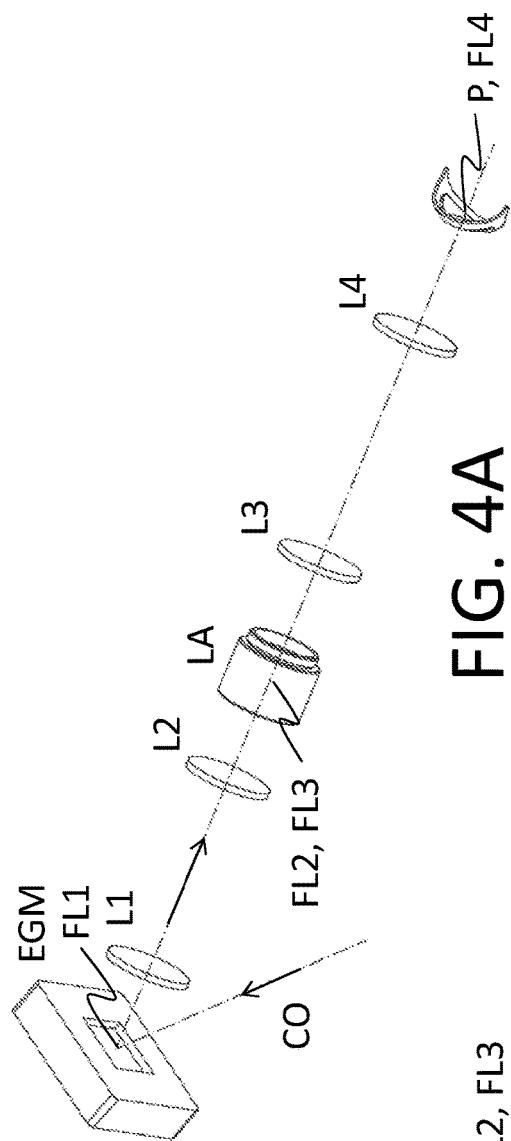
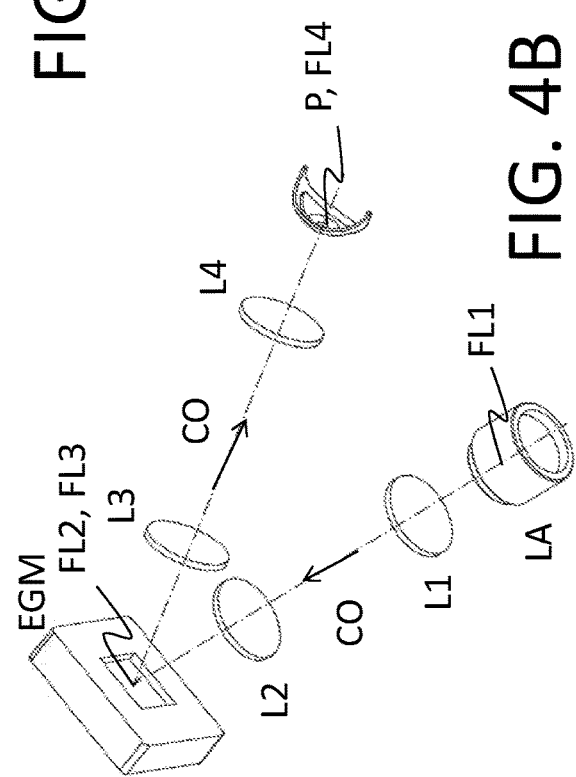
FIG. 4A
FIG. 4B

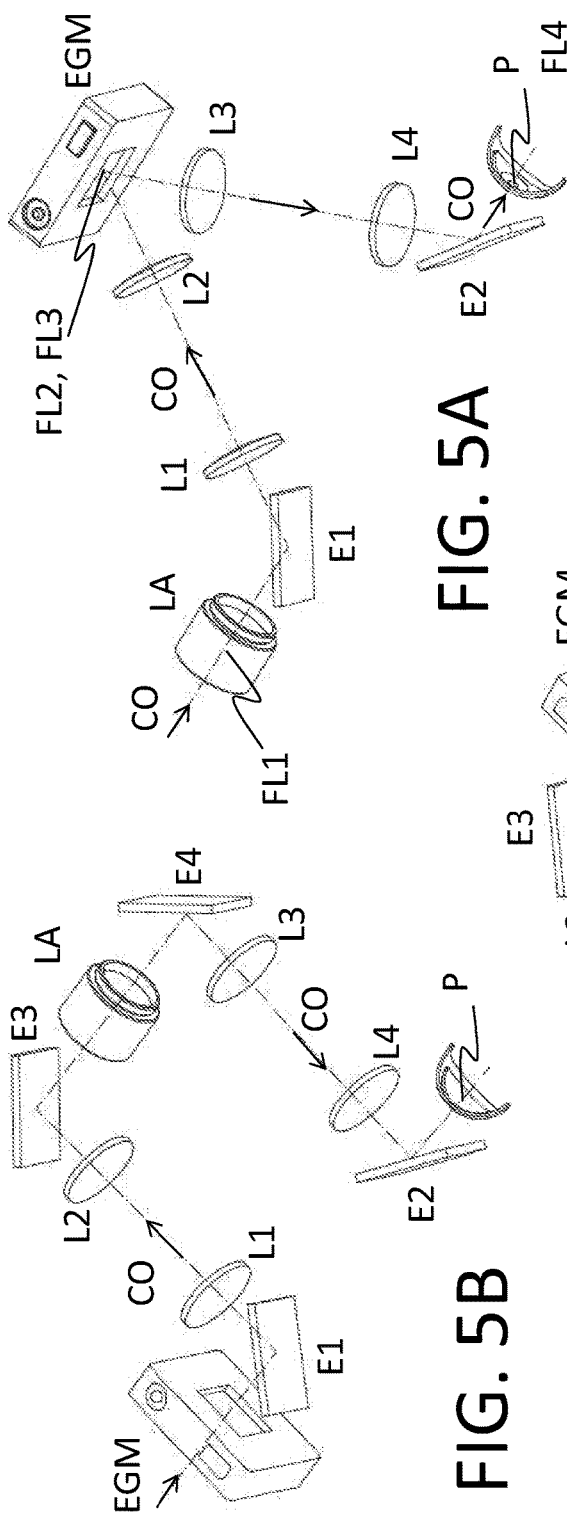
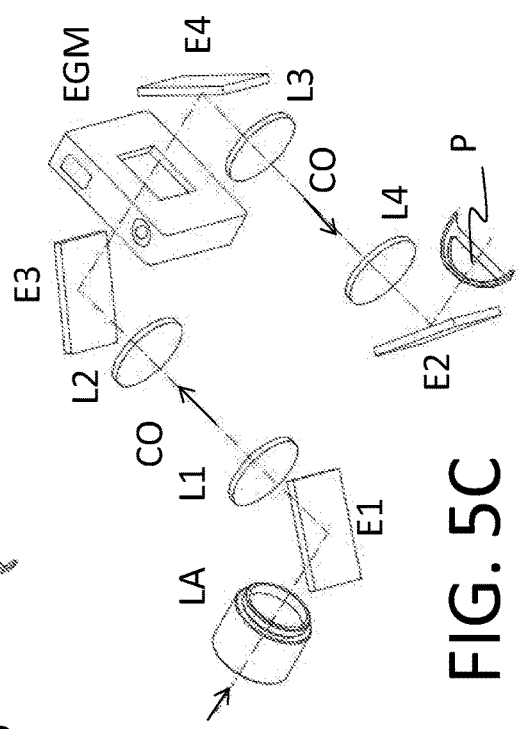
FIG. 5A
FIG. 5B
FIG. 5C

MINIATURISED INSTRUMENT FOR SIMULATING SIMULTANEOUS VISION BY GENERATING MASKS

FIELD OF THE INVENTION

The present invention relates, in general, to the field of ocular optics and, in particular, to the field of ophthalmic corrections to compensate for presbyopia.

STATE OF THE ART

The young human eye has the capacity of changing its focus to clearly see both far objects and near objects. This capacity of the eye, called accommodation, is achieved thanks to the lens being able to change its focus, changing the shape of its surfaces. Age-related loss of accommodation is called presbyopia. Presbyopia starts showing symptoms at around 45 years of age and means that the entire population above 55 depends of optical corrections of some kind to correctly see far and near. The most common correction of presbyopia are ophthalmic lenses, whether in the form of reading glasses, glasses with bifocal segments or progressive lenses. Despite the fact that glasses are the most immediate solution to the problem posed by presbyopia, glasses are far from being considered an optimal solution, for aesthetic questions or due to their inconvenience.

Various solutions to mitigate the effects of presbyopia are based on the concept of simultaneous vision. Simultaneous vision corrections superimpose two or more images on the retina, one of them corresponds to a far vision observation distance and another to a near vision observation distance. The resulting final image on the retina contains a sharp component, in focus, superimposed on other blurred components, out of focus, which produce a general loss of contrast. Not everyone is capable of tolerating simultaneous vision. For the adaptation of contact lenses it is typical that the patient tries different designs. The situation is much worse in the case of surgical solutions as they are irreversible processes. From here there arises the need to simulate simultaneous vision and provide the patient with the new visual experience before adaptations or surgeries. This is an ideal approach to anticipate and avoid the visual problems that each patient will have, whether optical or neuronal.

Spanish patent application with application number P201331436 proposed a new concept for the generation of simultaneous vision, called temporal channel multiplexing. It consists of inducing with an adjustable lens a periodical variation in the time in the vergence of the light beam that it traverses. The different vergence levels, which are periodically repeated, define different temporal channels that are temporarily multiplexed at a higher frequency than the eye fusion frequency, and the space-time superimposition of all the component images forms a final simultaneous vision image, which is perceived as static.

The invention disclosed in the aforementioned patent application makes use of the concepts of temporal multiplexing to simulate pure simultaneous vision, wherein the entire eye pupil acts at the same time as area of near vision and area of far vision. However, in many actual ophthalmic corrections designs of simultaneous vision (contact lenses, intraocular lenses) the pupil is divided in areas, segments, each one of which corresponds to a vision distance (near, intermediate, far). The present invention uses the terms "pupil patterns" to refer to the pupils divided into segments or areas of different powers.

The generation of pupil patterns, with different regions devoted to far, near or intermediate vision, can be performed by special light modulators (SLM) based on cells which produce a variable phase difference, often accompanied by changes in polarisation, in the light which hits them, in accordance with the voltage. The phase difference in each point is related to the level of each pixel, such that the map can be considered as an image, with a spatial resolution determined by the number of pixels. These SLMs can be incorporated in adaptive optics systems (Testing vision with radial and angularly segmented multifocal patterns using adaptive Optics. Maria Vinas, Carlos Dorronsoro, Veronica Gonzalez, Daniel Cortes, Susana Marcos. Investigative Ophthalmology & Visual Science June 2015, Vol.56, 1358, 2015), operating on the light reflection that hits them in what will be called reflection mode. Another previously presented configuration (Visual testing of segmented bifocal corrections with a compact simultaneous vision simulator, Carlos Dorronsoro, Aiswaryah Radhakrishnan, Pablo de Gracia, Lucie Sawides, José Ramón Alonso-Sanz, Daniel Cortés, Susana Marcos. Investigative Ophthalmology & Visual Science April 2014,Vol.55, 781, 2014) uses a SLM operating in transmission mode, operating on the light transmission, in combination with a two-channel simultaneous vision system previously presented (application P200930055), providing far and near pupil distributions, given by patterns defined in the SLM by binary images in white and black.

These simultaneous vision simulation methods are not suitable for compact clinical prototypes as they have great complexity, size and cost.

Another identified solution consists of the projection of a phase pattern in the pupil, constructed by microlithography or precision machining.

Other solutions are based on projecting an actual intraocular lens within the eye, by means of optical projector systems, (EP 2631891 A1; US 2011/0080562 A1). This approach requires having the different lenses and their variants with different parameters. Furthermore, it is necessary that the optical system is sophisticated, to eliminate the lens's optical power, which usually has a value close to 20 dioptres. The necessary securing of the lenses in a cell, for their projection, involves a handling time to physically place and remove the intraocular lens, which means that direct and immediate comparisons cannot be performed between different lenses, typical in stringent experiments of subjective preference. Although they have shown a viable approximation on laboratory systems, the existing systems to simulate pupil patterns are impractical in a robust and portable system, for the stated reasons. Furthermore, in a binocular system, wherein the visual simulation is performed in both eyes at the same time, the problem is multiplied.

The technical problem resolved in the present invention is the simulation of simultaneous vision in a compact instrument with the capacity of simulating programmable pupil patterns using a single spatial channel. As it does not resort to two or more spatial channels to resolve the problem the aforementioned drawbacks are eliminated.

DESCRIPTION OF THE INVENTION

In a first aspect of the invention, a miniaturised instrument for simulating simultaneous vision by generating masks is provided. The miniaturised instrument for simulating simultaneous vision by generating masks comprises: a mask-generating element (EGM) which generates at least two complementary masks, with a temporal frequency of alternation such that, sequentially, each mask lets an incident light from an object partially pass (i.e. through an area of the pupil), at the same time as the at least one other mask (i.e. the other masks) partially blocks (i.e. in the other areas of the pupil) the incident light; an adjustable lens of variable optical power which generates, with the temporal frequency of alternation, at least two different optical powers corresponding to at least two observation distances; wherein the mask-generating element and the adjustable lens are located in a single optical channel via which the incident light circulates, such that each mask of the mask-generating element (EGM) is temporally synchronised with each power of the adjustable lens, obtaining, via high-speed temporal fusion, a combined pupil pattern of at least two observation distances. The combination of all the masks and optical powers produce, by high-speed temporal fusion, a pupil pattern combining at least two optical powers corresponding to at least two observation distances.

In a particular embodiment, the miniaturised instrument for simulating simultaneous vision by generating masks comprises: a mask-generating element (EGM) which generates, with a temporal frequency of alternation, two complementary masks such that when, sequentially, one lets an incident light from an object partially pass, the other partially blocks the incident light, and vice-versa; an adjustable lens of variable optical power which generates, with the temporal frequency of alternation, two different optical powers corresponding to two observation distances; wherein the mask-generating element and the adjustable lens are located in a single optical channel via which the incident light circulates, such that each mask of the mask-generating element (EGM) is temporally synchronised with a power of the adjustable lens, obtaining a pupil pattern by temporal fusion combining two observation distances.

In another particular embodiment, the miniaturised instrument for simulating simultaneous vision by generating masks comprises: a mask-generating element (EGM) which generates, with a temporal frequency of alternation, at least three complementary masks such that when, sequentially, one lets the incident light from an object partially pass, the at least two other masks partially block the incident light; an adjustable lens of variable optical power which generates, with the temporal frequency of alternation, at least three different optical powers corresponding to at least three observation distances; wherein the mask-generating element and the adjustable lens are located in a single optical channel via which the incident light circulates, such that each mask of the mask-generating element (EGM) is temporally synchronised with a power of the adjustable lens, obtaining a pupil pattern by temporal fusion combining at least three observation distances.

In the present invention, complementary masks are understood to be those masks which jointly disposed cover the entire pupil. In all the examples of embodiment, a mask lets the light partially pass (it lets the light pass through an area of the pupil) and the other masks block the light partially (through the other areas of the pupil) for a determined time instant. In the following time instant (equivalent to the inverse of the frequency of alternation), the mask which let the light pass blocks it, one of those which blocked the light lets it pass and the other masks continue blocking the light. And so on and so forth. This defines "sequentially".

To produce the visual experience of simultaneous vision without observing vibration or flickering of the image, the frequency of alternation of the different masks and powers must be greater than the frequency of fusion of the visual system. In one embodiment of the invention, the frequency of alternation is preferably greater than 30 Hz, and more preferably greater than 60 Hz.

The optical channel contains the incident light from an observed object whose propagation direction comes from the observed object until reaching the observer's or patient's eye. Bearing in mind this light transmission direction, it defines for all forms of embodiment of the invention, as front focus of a lens, the focus thereof which is reached by the incident light before traversing the lens and as rear focus of a lens, the focus thereof which is reached by the incident light after traversing the lens.

The image in the retina or retinal image is formed when the light from an object traverses the pupil pattern and the lens of the eye makes it converge in the retina. The present invention achieves that, on an observer or patient's eye placed in the plane containing the pupil pattern, an image is generated on the retina (retinal image) which is the combination (multiplexing) of several images corresponding to different observation distances. This retinal image is an image of static appearance in the retina, multifocal in nature and, therefore, with a certain degradation. This retinal image simulates the one produced by a real correction since it is equivalent to it, for all intents and purposes.

As previously mentioned, for the present invention, the masks let the light pass through some areas and not through others. These areas are also called segments. The masks are generated by the Mask-Generating Element (EGM). Technologically, the Mask-Generating Element (EGM) is achieved by means of a programmable active optical element which may function by: i) transmission: a transparent material that lets the light be transmitted in some areas and not in others; or, ii) by reflection, a specular material which in some areas reflects and not in others. The EGM in transmission can be achieved by means of a spatial light modulator based on a liquid crystal technology, operating in transmission, whilst the EGM in reflection mode can be achieved by means of a spatial light modulator of reflection light or with a digital micromirror device. The combination of all the masks (EGM) and all the powers (LA) by temporal multiplexing produces a pupil pattern which is projected in the pupil of the patient's eye and which produces the optical effect of a multifocal simultaneous vision correction: retina images (retinal images) which have superimposed focussed and blurred components. In other words, the light, according to the area of the pupil wherethrough it passes, produces a more or less focussed component image in the retina. The superimposition in the retina of the component images, all of the same size, produces that each point of the image is focussed and blurred at the same time, as occurs in real ophthalmic simultaneous vision corrections.

In another particular embodiment, the miniaturised instrument for simulating simultaneous vision by generating masks additionally comprises two projector lenses, both with the same focal length and separated from one another by two focal lengths. The instrument configured such that the mask-generating element is located in the front focus of one of the lenses, and the adjustable lens (LA) is approximately placed in the rear focus of the other lens, forming the pupil pattern on the rear focus of the other lens.

In another particular embodiment, the miniaturised instrument for simulating simultaneous vision by generating masks additionally comprises two projector lenses with the same focal length and separated from one another by two focal lengths. The instrument configured such that the adjustable lens is located in the front focus of one of the lenses and the mask-generating element is approximately placed in the rear focus of the other lens, forming the pupil pattern on the rear focus of the other lens.

In another particular embodiment, the miniaturised instrument for simulating simultaneous vision by generating masks additionally comprises two projector lenses with the same focal length and separated from one another by two focal lengths. The instrument configured such that the adjustable lens (LA) and the mask-generating element (EGM) is located in the front focus of one of the lenses, and the pupil pattern is formed on the rear focal plane of the other lens.

In another particular embodiment, the miniaturised instrument for simulating simultaneous vision by generating masks additionally comprises four projector lenses, two end and two intermediate, with the same focal length, consecutively distributed on the optical channel and with a separation between each two consecutive lenses equivalent to two focal lengths. The instrument configured such that the mask-generating element (EGM) is located in the front focus of one of the end lenses, the adjustable lens (LA) is located in the rear focus of one of the intermediate lenses which coincides with the front focus of the other intermediate lens, and the pupil pattern is formed on the rear focus of the other end lens. The mask-generating element (EGM) can be located non-perpendicularly to the optical channel, such that the mask-generating element (EGM), operating in reflection mode, directly receives the incident light and reflects it in another direction, wherein it traverses the four projector lenses and the adjustable lens (LA).

In another particular embodiment, the miniaturised instrument for simulating simultaneous vision by generating masks additionally comprises four projector lenses, two end and two intermediate, with the same focal length, consecutively distributed on the optical channel (CO) and with a separation between each two consecutive lenses equivalent to two focal lengths. The instrument configured such that the adjustable lens (LA) is located in the front focus of one of the end lenses, the mask-generating element (EGM) is located in the rear focus of one of the intermediate lenses which coincides with the front focus of the other intermediate lens, and the pupil pattern is formed on the rear focus of the other end lens. The mask-generating element (EGM) can be located non-perpendicularly to the optical channel, such that the mask-generating element (EGM), operating in reflection mode, receives the incident light through the adjustable lens (LA), of an end lens and an intermediate lens, and reflects it in another direction, wherein it traverses an intermediate lens and an end lens.

In another particular embodiment, the miniaturised instrument for simulating simultaneous vision by generating masks additionally comprises: four projector lenses, two end and two intermediate, with the same focal length, consecutively distributed on the optical channel and with a separation between each two consecutive projector lenses equivalent to two focal lengths; and two end mirrors. The instrument is configured such that the incident light runs consecutively through: the adjustable lens (LA), an end mirror, an end lens, an intermediate lens, the mask-generating element (EGM) in reflection mode, the other intermediate lens, the other end lens and the other mirror, until reaching the pupil plane, where the rear focus of the other end lens can be found.

In another particular embodiment, the miniaturised instrument for simulating simultaneous vision by generating masks additionally comprises: four projector lenses, two end and two intermediate, with the same focal length, consecutively distributed on the optical channel and with a separation between each two consecutive projector lenses equivalent to two focal lengths; two end mirrors and two intermediate mirrors. The instrument is configured such that the incident light runs consecutively through: the mask-generating element (EGM), an end mirror, an end lens, an intermediate lens, an intermediate mirror, the adjustable lens, the other intermediate mirror, the other intermediate lens, the other end lens and the other end lens until reaching the pupil plane, where the rear focus of the other end lens can also be found.

In another particular embodiment, the miniaturised instrument for simulating simultaneous vision additionally comprises: four projector lenses, two end and two intermediate, with the same focal length, consecutively distributed on the optical channel and with a separation between each two consecutive projector lenses equivalent to two focal lengths; two end mirrors and two intermediate mirrors. The instrument is configured such that the incident light runs consecutively through: the adjustable lens (LA), an end mirror, an end lens, an intermediate lens, an intermediate mirror, the mask-generating element (EGM), the other intermediate mirror, the other intermediate lens, the other end lens and the other end lens until reaching the pupil plane, where the rear focus of the other end lens can also be found.

In another particular embodiment, the miniaturised instrument for simulating simultaneous vision additionally comprises: four projector lenses, two end and two intermediate, with the same focal length; two end mirrors and two intermediate mirrors; and, a double mirror (two opposite sides). The instrument is configured such that the incident light consecutively runs through one side of the double mirror, the adjustable lens, an end mirror, an end lens, an intermediate mirror, an intermediate lens, the mask-generating element (EGM), the other lens, the other intermediate mirror, the other end lens, the other end lens and the other side of the double mirror until reaching the pupil plane, where the rear focus of the other end lens can also be found. The human eye is, therefore, co-aligned with the incident light.

In another particular embodiment, the miniaturised instrument for simulating simultaneous vision additionally comprises: four projector lenses, two end and two intermediate, with the same focal length; two end mirrors; and a double mirror (two opposite sides). The instrument is configured such that the incident light consecutively runs through one side of the double mirror, the adjustable lens, an end mirror, an end lens, an intermediate lens, the mask-generating element (EGM), the other intermediate lens, the other end lens, the other end lens and the other side of the double mirror until reaching the pupil plane, where the rear focus of the other end lens can also be found. The human eye is, therefore, co-aligned with the incident light.

In another particular embodiment, the miniaturised instrument for simulating simultaneous vision it additionally comprises: four projector lenses, two end and two intermediate, with the same focal length; two end mirrors; and a double mirror (two opposite sides). The instrument is configured such that the incident light consecutively runs through the adjustable lens (LA), one side of the double mirror, an end mirror, an end lens, an intermediate lens, the mask-generating element (EGM), the other intermediate lens, the other end lens, the other end lens and the other side of the double mirror, until reaching the pupil plane, where the rear focus of the other end lens can also be found. The human eye is, therefore, co-aligned with the incident light.

In a second aspect of the invention, it provides the use of the instrument according to one or more previous embodiments in combination with glasses, contact lenses, intraocular lenses, refractive surgery or other ophthalmic or surgical corrections.

In a third aspect of the invention, it provides the use of the instrument according to one or more previous embodiments as phoropter.

In a fourth aspect of the invention, it provides the use of the instrument according to one or more previous embodiments in combination with visual or psychophysical tests.

In a fifth aspect of the invention, it provides the use of the instrument according to one or more previous embodiments to assess the tolerance of patients to simultaneous vision corrections or for the training of the patient prior to the implantation of simultaneous vision corrections.

DESCRIPTION OF THE FIGURES

FIGS. 1A and 1B show different examples of embodiment of the invention to generate the pupil pattern by multiplexed combination of a mask-generating element and an adjustable lens.

FIGS. 4A and 4B show two examples of embodiment of the present invention with a mask-generating element, an adjustable lens and four lenses configured in an optical channel incorporating a reflection on the mask-generating element, for different combinations of the lenses, the adjustable lens and the mask-generating element.

FIG. 5A shows an example of embodiment of the present invention with a Mask-Generating Element, an adjustable lens, four lenses and two mirrors configured in an optical channel in reflection on the Mask-Generating Element.

FIGS. 5B and 5C show two examples of embodiment of the present invention with a Mask-Generating Element, an adjustable lens, four lenses and four mirrors configured in an optical channel in reflection on the mirrors for different combinations of the lenses, the adjustable lens, the mirrors and the Mask-Generating Element.

EXAMPLE OF EMBODIMENT OF THE INVENTION

Figure 1B:
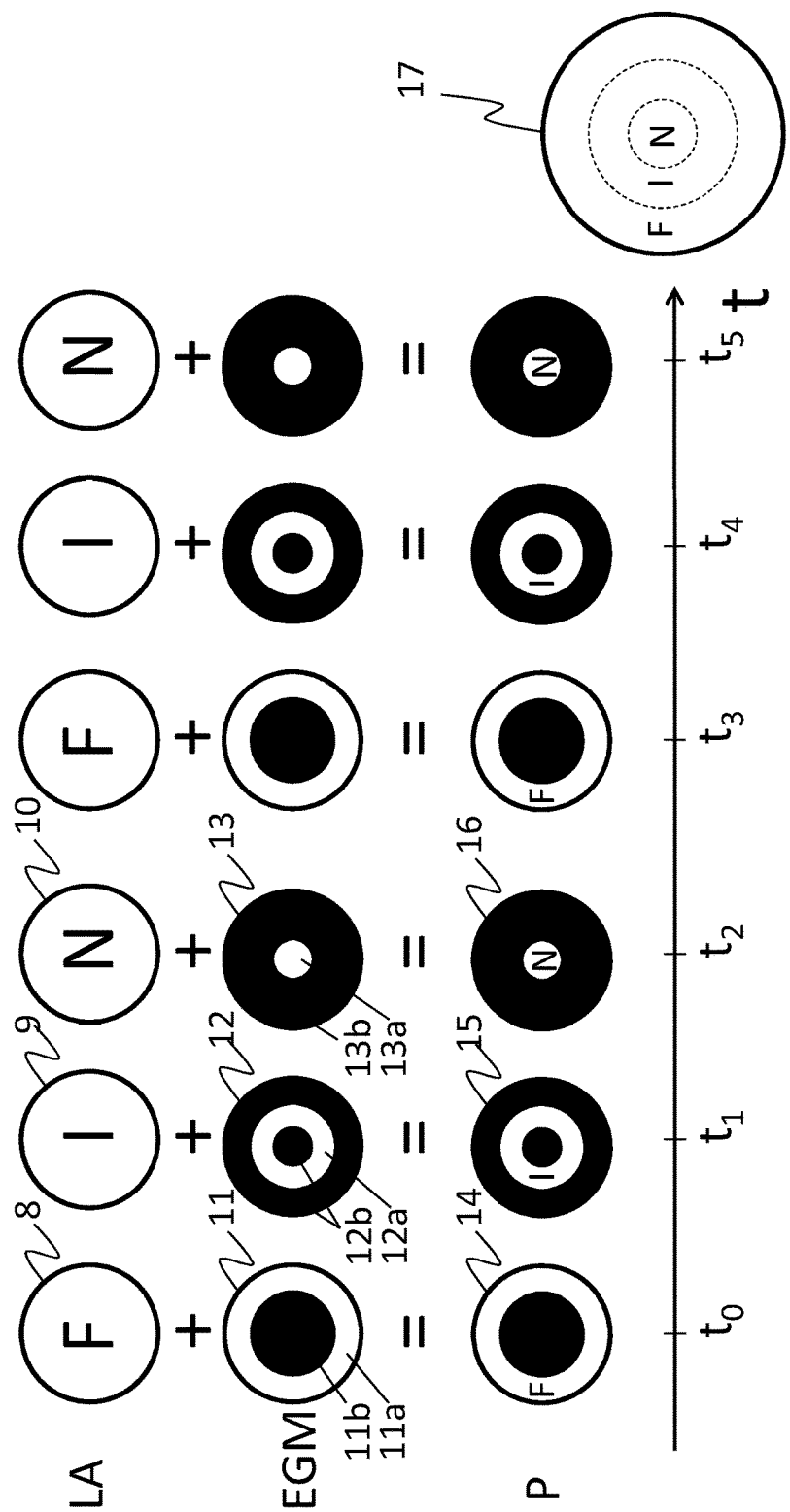

Several examples of embodiment of the present invention shall be described in detail below, with reference hereinafter to attached figures, wherein preferred embodiments of the invention are shown. However, the invention can be materialised in many different forms and should not be interpreted as limiting of the embodiments stated in the document; additionally, these embodiments are provided so that this explanation shall be detailed and complete, and shall completely transmit the field of the invention to persons skilled in the art. The same numbers and same letters refer to the same elements throughout the document.

The present disclosure provides novel solutions for the simulation of simultaneous vision applied to presbyopia. Advantageously, the present invention is capable of being implemented in miniaturised devices since it only uses one channel to form the pupil image. In general terms, the image in the retina or retinal image is formed when the light from an object travels through the lens of the eye which makes it converge on the retina, forming the image of the object in the retina. This retinal image can be focussed or blurred. In the present invention, the light from the object forms the retinal image after traversing the pupil pattern generated by the LA and the EGM, which is projected in the eye pupil. The present invention achieves that in the retina of an observer's or patient's eye, placing the eye in a position such that the pupil coincides with the plan containing the pupil pattern "P" of the instrument, a retinal image is generated which is the combination (multiplexing) of several images corresponding to different observation distances (e.g. far vision and near vision).

FIG. 1A shows an example of embodiment of the invention to generate the pupil pattern 7. FIG. 1A shows an adjustable lens LA (of variable focus) which changes its optical power every certain time interval (determined by a frequency of alternation) alternating between the power corresponding to a far vision F (1) and a near vision N (2). The adjustable lens LA is temporally synchronised with a Mask-Generating Element EGM which has, for the embodiment of the invention shown in FIG. 1A, two semi-circular segments 3a and 3b which are complemented to cover the entire circular light beam, but such that when a segment blocks the incident light from an observed object (not shown in the figures), the other segment lets the incident light pass, and vice-versa. These two combinations of the segments give rise to two different masks (3,5). Therefore, at a certain time instant to, the adjustable lens LA, of variable focus, has a power corresponding to far vision F, and the EGM provides a semi-circular pupil mask which blocks the left semicircle of the incident light. By means of optical projections with a single optical channel, the EGM and the LA coincide in a single plane called pupil plane P because it is the plane wherein the eye pupil is placed. This projection which combines masks of the EGM and optical power of the LA gives rise in the pupil plane P to a transitory pupil pattern 4 containing an opaque semi-circular half (by the blocking of the segment) and another semi-circular half wherethrough a retinal image corresponding to far vision is formed. In the following time instant $t_1$, the adjustable lens LA has a power corresponding to near vision N, and the mask-generating element EGM provides a semi-circular pupil mask which blocks the right semicircle of the incident light which, through the same front optical channel, traverses the adjustable lens LA and the mask-generating element EGM, thus projecting a pupil pattern 6 (pupil plane P) containing an opaque semi-circular half (due to the blocking of the segment) and another semi-circular half through which a retinal image corresponding to near vision is formed. In the following time instant $t_2$, it repeats the same configuration of the adjustable lens LA and of the mask-generating element EGM that it had for $t_0$. In the following time instant $t_3$, it repeats the same configuration of the adjustable lens LA and of the EGM it had for $t_1$.

This alternate repetition of the configurations in time (temporal multiplexing), performed with a frequency greater than the flicker fusion threshold of a person's eye, means that the pupil of that person forms a complete pupil pattern 7 (pattern of segments that cover the entire pupil) which in this example is the combination of two transitory semicircular pupil patterns 4 and 6 corresponding to two different observation distances (near vision and far vision). In other words, the complete pupil pattern is the combination of two transitory pupil patterns. The present invention uses the "frequency of alternation" to define the alternate repetition of the configurations. In the configuration shown in FIG. 1A, there are only two pupil segments (masks) corresponding to two observation distances, i.e. it simulates a two-segment bifocal lens in semicircle, but the number of configurations can be any other for the person skilled in the art. With the same methodology, it is possible to generate complete bifocal pupil patterns with different angles in the line which separates the semicircles. It is also possible to generate complete bifocal pupil patterns of different forms to that shown in the example, e.g. annular or radial patterns or a combination of both. It is also possible to generate trifocal patterns, which include intermediate areas of vision (see FIG. 1B). In general, pupil patterns can be generated with any number of foci, with any form and distribution of the pupil segments.

FIG. 1B shows an example of embodiment of the invention to generate the pupil pattern 17. FIG. 1B shows an adjustable lens LA (of variable focus) that changes its optical power every certain time interval (determined by a frequency of alternation; $\Delta t = 1/f_{afternation}$) alternating between the power corresponding to far vision F (8), intermediate vision I (9) and near vision N (10). The adjustable lens LA is temporally synchronised with a Mask-Generating Element EGM which has, for the embodiment of the invention shown in FIG. 1B, three segments 11a (outer and annular), 12a (intermediate and annular) and 13a (central and circular) which are complemented to cover the entire circular light beam, but such that when a segment lets the incident light pass, the other two segments block the incident light from an observed object (not shown in the figures) thus forming a different mask for each combination of the segments (11, 12, 13). Therefore, at the time instant $t_0$, the adjustable lens LA, of variable focus, has a power corresponding to far vision F, and the EGM provides an annular pupil mask which lets the light pass through the outer segment 11a, of annular form. For this, the outer segment 11a lets the light pass and the intermediate 12a and central segments 13a block the incident light. The intermediate 12a and central segments 13a when they jointly block the light are referenced as a single segment 11b for $t=t_0$. By means of optical projections with a single optical channel, the EGM and the LA coincide in a single plane, which we call pupil plane P because it is the plane wherein the eye pupil is placed. This projection which combines masks of the EGM and optical power of the LA gives rise in the pupil plane P to a transitory pupil pattern 14 containing a circular area which blocks the light by 40%, and an annular area which lets 60% of the light pass, wherethrough a retinal image corresponding to far vision shall be formed. In the following time instant $t_1$, the adjustable lens LA has a power corresponding to intermediate vision I (9), and the mask-generating element EGM provides an intermediate annular pupil mask where the intermediate segment 12a lets 30% of the light pass at the same time as the central 13a and outer segments 11a (segments 13a and 11a are jointly referenced as 12b in $t=t_1$) block the incident light by 70% which, through the same front optical channel, traverses the adjustable lens LA and the mask-generating element EGM, thus projecting a pupil pattern 15 (pupil plane P) containing two opaque areas corresponding to the outer and central segments, and an intermediate annular area wherethrough a retinal image corresponding to intermediate vision will be formed. In the following time instant $t_2$, the adjustable lens LA has a power corresponding to near vision N (10), and the mask-generating element EGM provides a pupil mask which only lets 10% of the incident light pass. The circular incident light through the same front optical channel, traverses the adjustable lens LA and the mask-generating element EGM, thus projecting a pupil pattern 16 (pupil plane P) containing an opaque annular area which occupies 90% (by the blocking of segments 11a, 12a, jointly referenced as 13b in $t=t_2$) and a circular area which occupies 10% wherethrough a retinal image corresponding to near vision shall be formed. In the following time instant $t_3$ the same configuration of the adjustable lens LA and the mask-generating element EGM it had for to is repeated. In the following time instant $t_4$ the same configuration of the adjustable lens LA and the EGM it had for $t_1$ is repeated. And so on and so forth.

As regards the optical system which provides the configuration described in FIG. 1A and/or 1B of the adjustable lens LA and the mask-generating element EGM, there are different configurations or examples of embodiment according to the needs of the miniaturised instrument for simulating simultaneous vision.

Some of the possible configurations or examples of embodiment are described below.

The simultaneous vision simulating instrument is miniaturised as a consequence of the configuration in a single optical channel which can be straight or non-straight. In this last case, the incorporation of mirrors in the instrument enables bending the optical path, which contributes to miniaturisation of the instrument.

Figure 2A:
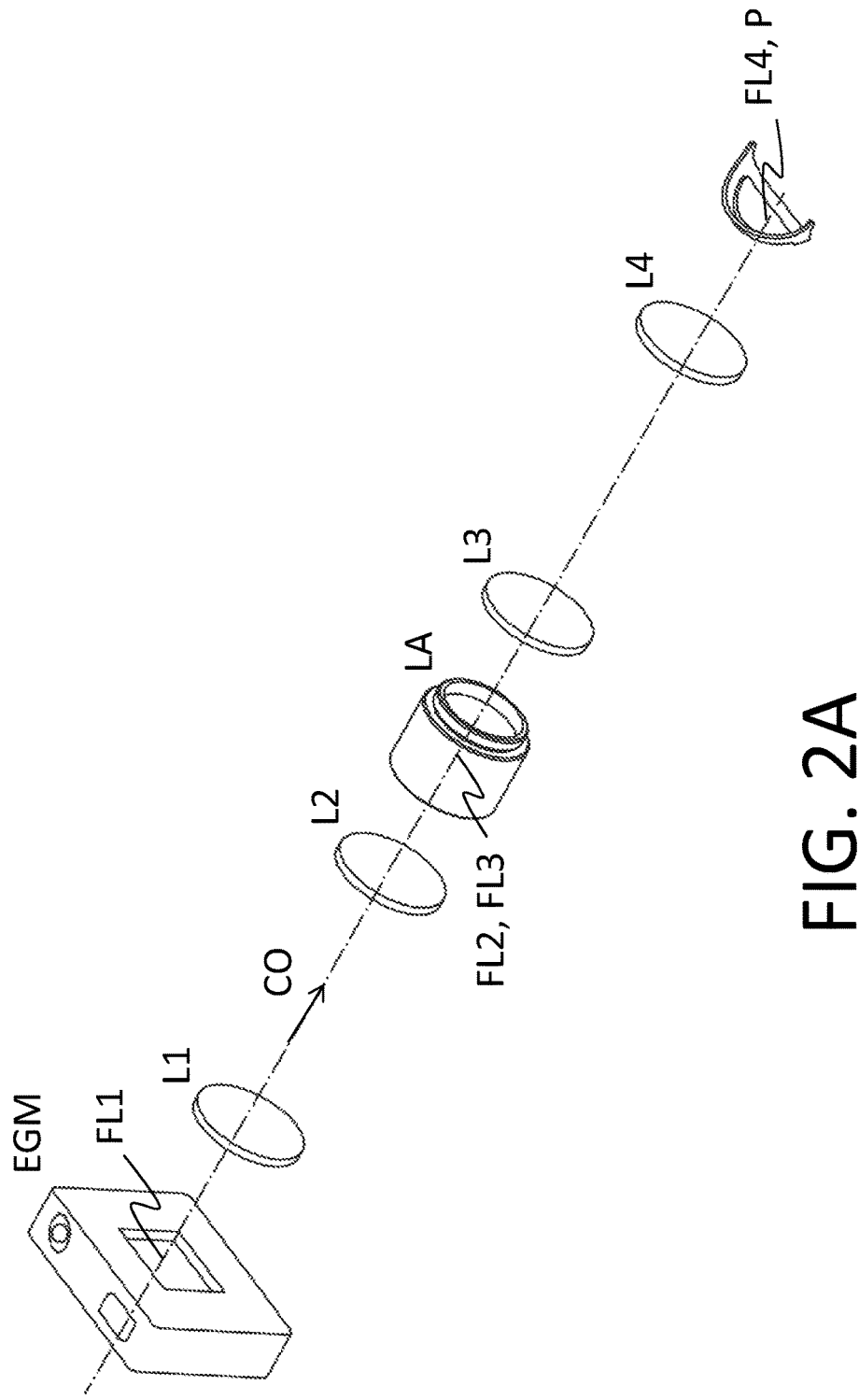
FIGS. 2A and 2B show two examples of embodiment of the present invention with a mask-generating element, an adjustable lens and four lenses configured in a straight optical channel for different disposals of the adjustable lens and mask-generating element.
Figure 2B:
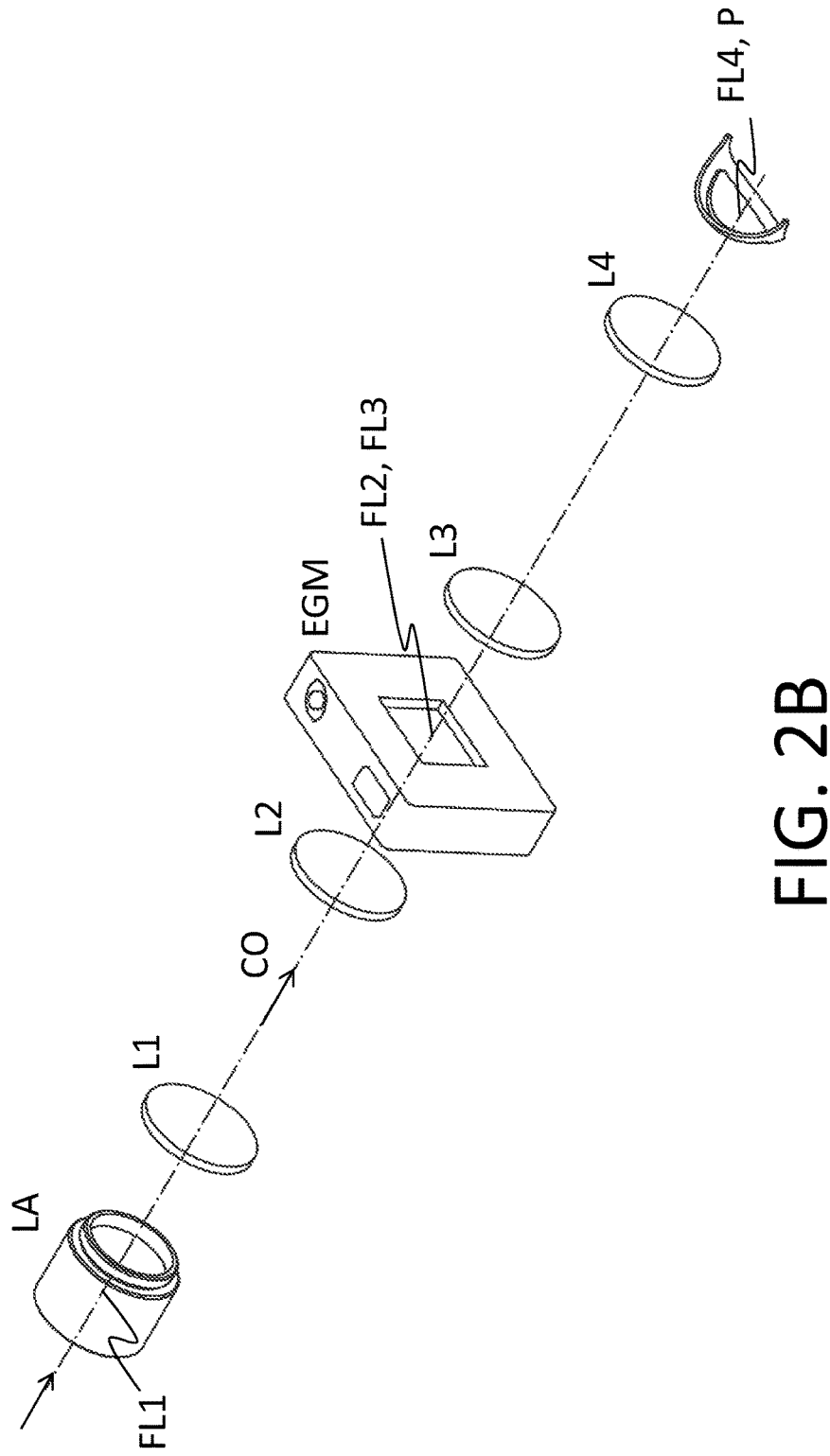

The examples of embodiment described below use different optical projection methods based on projections with pairs of lenses, considering their properties and limitations. Thus, in a projection system with two lenses with equal focal lengths and separated from one another by two focal lengths, an optical object or element placed in the front focus of one of the lenses is projected in the rear focus of the other lens, where the other optical element may be placed or in a user's eye. In this configuration the image is inverted. To resolve it, two additional lenses can be added to the instrument that form another projection system, which cancel the previous inversion, as shown in FIGS. 2A and 2B. But introducing additional lenses implies that the instrument requires greater length which must be added to the natural reading distance, and therefore it is severely altered.

FIG. 2A shows an example of embodiment of the present invention where the miniaturised instrument for simulating simultaneous vision by generating masks has a Mask-Generating Element EGM, an adjustable lens LA, of variable focus, and four projector lenses L1, L2, L3 and L4 configured in a single straight optical channel CO. In the implementation shown in FIG. 2A, the incident light from the observed object (not shown in the figure), which travels through the optical channel in the direction shown in FIG. 2A, consecutively traverses the EGM, the end lens L1, the intermediate lens L2, the adjustable lens LA, the intermediate lens L3 and finally the end lens L4 until reaching the pupil plane P where it projects the complete pupil pattern as described in the example of embodiment of FIG. 1A-1B. The lenses L1, L2, L3 and L4 have the same focal length. The separation between each two consecutive projector lenses is equivalent to two focal lengths, such that the mask-generating element EGM is located in the focal plane front FL1 of the end lens L1. The adjustable lens LA is located in the rear focus FL2 of the lens L2 which coincides with the front focus FL3 of the lens L3. Finally, the pupil pattern P is projected on the rear focal plane FL4 of the other end lens L4.

FIG. 2B shows an example of embodiment of the present invention where the miniaturised instrument for simulating simultaneous vision by generating masks has a Mask-Generating Element EGM, an adjustable lens LA, of variable focus, and four projector lenses L1, L2, L3 and L4 configured in a single straight optical channel CO. In the implementation shown in FIG. 2B, the incident light from the observed object, which travels through the optical channel according to the direction shown in FIG. 2B, consecutively traverses the adjustable lens LA, the end lens L1, the intermediate lens L2, the mask-generating element EGM, the intermediate lens L3 and finally the end lens L4 until reaching the pupil plane P where it projects the complete pupil pattern as described the example of embodiment of FIG. 1A to-1B. The four projector lenses L1, L2, L3 and L4 have the same focal length. The separation between each two consecutive lenses is equivalent to two focal lengths, such that the adjustable lens LA is located in the front focus FL1 of the end lens L1, the mask-generating element EGM is located in the rear focus FL2 of the intermediate lens FL2 which coincides with the front focus FL3 of the intermediate lens L3. Finally, the pupil pattern P is projected on the rear focal plane FL4 of the other end lens L4.

Figure 3A:
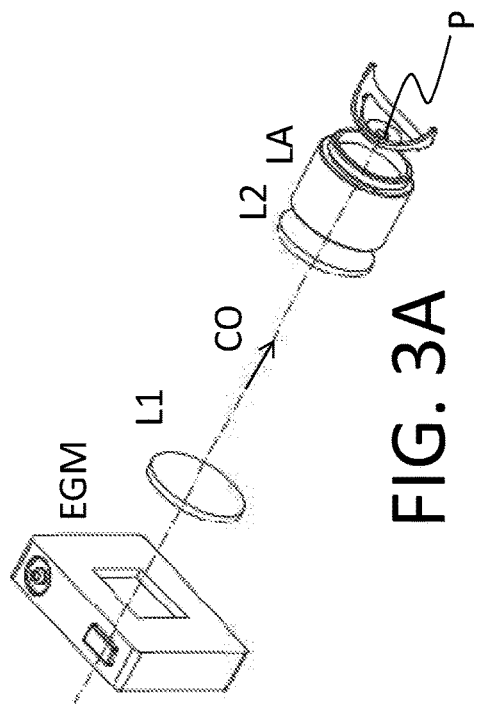
FIGS. 3A, 3B and 3C show three examples of embodiment of the present invention with a mask-generating element, an adjustable lens and two lenses configured in a straight optical channel for different combinations of the adjustable lens and mask-generating element.
Figure 3C:
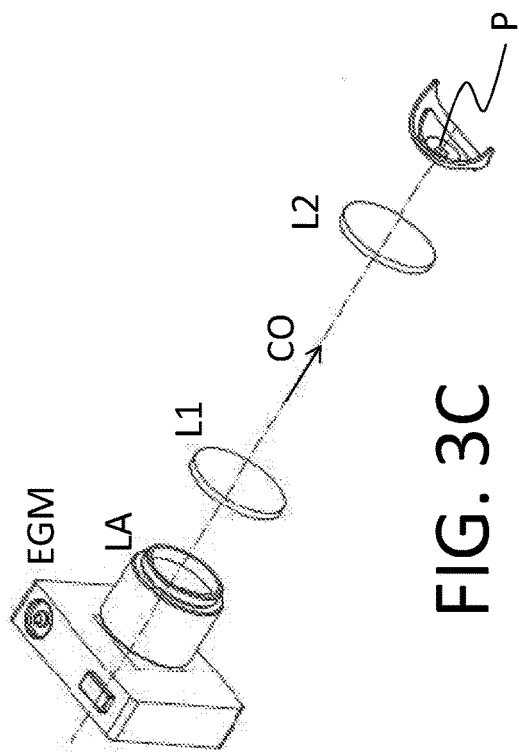
Figure 3B:
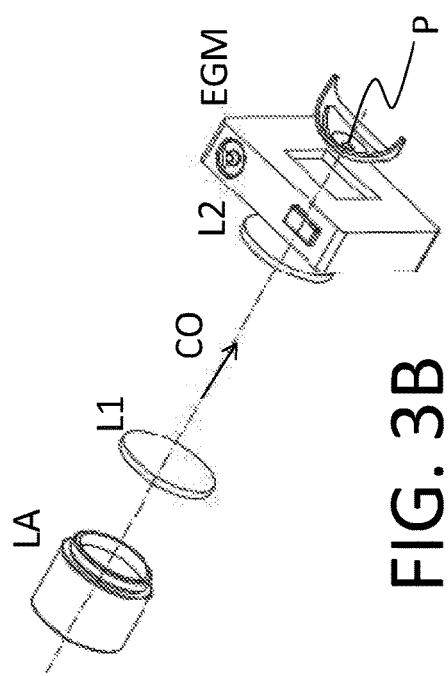

When the user uses the instrument described in FIGS. 2A or 2B to observe a near object, the reading distance is greatly altered due to the length of the instrument and to the use of four projector lenses. So that the reading distance is less affected, it is possible to use different implementations based on the use of just two single projection lenses. Three of these configurations are shown in FIGS. 3A, 3B and 3C. In FIG. 3A, an EGM is positioned in transmission mode in the front focus of a projection lens, and the adjustable lens LA is placed in the plane as close as possible to the pupil plane P, in the rear focus of the other lens (the eye pupil is located in P, and for this reason the LA may be close to, but not exactly on, the pupil plane P). In FIG. 3B, the same solution as in FIG. 3A, but exchanging the EGM for the adjustable lens. In FIG. 3C, the two elements EGM and LA are approximately position in the front focus of the first projection lens.

FIG. 3A shows an example of embodiment of the present invention where the miniaturised instrument for simulating simultaneous vision by generating masks has a mask-generating element EGM, an adjustable lens LA, of variable focus, and two projector lenses L1 and L2, configured in a single straight optical channel CO. In the implementation shown in FIG. 3A, the incident light from the observed object (not shown in the figure), which travels through the optical channel CO in the direction shown in FIG. 3A, consecutively traverses the mask-generating element EGM, the lens L1, the lens L2 and the adjustable lens LA, until reaching the pupil plane P where it projects the complete pupil pattern as described in the example of embodiment of FIG. 1A-1B. The lenses L1 and L2 have the same focal length. The separation between the lenses L1 and L2 is equivalent to two focal lengths, such that the mask-generating element EGM is located in the front focus FL1 of the lens L1, the complete pupil pattern is formed on the pupil plane P which coincides with the rear focal plane of lens L2, and the adjustable lens LA is approximately located in the rear focus FL2 of the lens L2.

FIG. 3B shows an example of embodiment of the present invention where the miniaturised instrument for simulating simultaneous vision by generating masks has a mask-generating element EGM, an adjustable lens LA of variable focus, and two projector lenses L1 and L2, configured in a single straight optical channel CO. In the implementation shown in FIG. 3B, the incident light from the observed object (not shown in the figure) and which travels in the direction shown in FIG. 3B through the optical channel CO, consecutively traverses the adjustable lens LA, the projector lens L1, the projector lens L2 and the mask-generating element EGM, until reaching the pupil plane P where it projects the complete pupil pattern as described in the example of embodiment of FIG. 1. The projector lenses L1 and L2 have the same focal length. The separation between the lenses L1 and L2 is equivalent to two focal lengths, such that the adjustable lens LA is located in the front focus FL1 of the lens L1, the complete pupil pattern is formed on the pupil plane P is projected on the rear focal plane of lens L2, and the mask-generating element EGM is approximately located in the rear focus FL2 of the lens L2.

FIG. 3C shows an example of embodiment of the present invention where the miniaturised instrument for simulating simultaneous vision by generating masks has a mask-generating element EGM, an adjustable lens LA of variable focus, and two projector lenses L1 and L2, configured in a single straight optical channel CO. In the implementation shown in FIG. 3C, the incident light from the observed object (not shown in the figure) and which travels in the direction shown in FIG. 3C through the optical channel CO, consecutively traverses the mask-generating element EGM, the adjustable lens LA, the projector lens L1 and the projector lens L2, until reaching the pupil plane P where it projects the complete pupil pattern as described in the example of embodiment of FIG. 1A-1B. The projector lenses L1 and L2 have the same focal length. The separation between the lenses L1 and L2 is equivalent to two focal lengths. The mask-generating element EGM and the adjustable lens LA are approximately located in the front focus of the lens L1. The complete pupil pattern P is projected on the rear focal plane of the lens L2. The LA and the EGM can exchange their positions, providing a similar configuration.

As only two projection lenses are used in the examples of FIGS. 3A, 3B and 3C, the projection and superimposition of elements is not as accurate as in the examples of FIGS. 2A and 2B, but it may constitute a sufficiently good approximation. Furthermore, with the use of single two projection lenses in the examples of FIGS. 2A, 2B and 2C an inversion is introduced in the image, which may be compensated by introducing mirrors or rectifier prisms in the system (something not shown in the figures).

In the examples of embodiment shown in FIGS. 2A, 2B, 3A, 3B and 3C, the optical channel is straight and all the elements (EGM, LA, projector lenses) placed on the optical channel are located in a line which passes through P, the plane wherein the pupil of the user's eye is located. Likewise, the mask-generating element EGM in the embodiments shown in FIGS. 2A, 2B, 3A, 3B and 3C operates in transmission mode. Other forms of embodiment of the invention are described below where the optical channel undergoes different reflections to optimise space and, therefore, the design of the miniaturised instrument of the present invention. Some of these reflections are produced by an EGM operating in reflection mode.

FIG. 4A shows an example of embodiment of the present invention where the miniaturised instrument for simulating simultaneous vision by generating masks has a Mask-Generating Element EGM, an adjustable lens LA, two end lenses L1 and L4 and two intermediate lenses L2 and L3 configured in a single optical channel CO. The Mask-Generating Element EGM operates in reflection mode in the present example of embodiment, which conditions the disposal of the other instrument elements. In the implementation shown in FIG. 4A, the incident light, which travels through the optical channel CO in the direction shown in FIG. 4A, non-perpendicularly hits the mask-generating element EGM, which reflects the incident light so that it consecutively traverses the end lens L1, the intermediate lens L2, the adjustable lens LA, the intermediate lens L3 and finally the end lens L4 until reaching the pupil plane P where it projects the complete pupil pattern as described in the example of embodiment of FIG. 1A-1B. All the projector lenses L1, L2, L3 and L4 have the same focal length. The separation between each two consecutive projector lenses is equivalent to two focal lengths, such that the mask-generating element EGM is located in the front focus FL1 of the end lens L1, the adjustable lens LA is located in the rear focus FL2 of the intermediate lens L2 which coincides with the front focus FL3 of the intermediate lens L3. The complete pupil pattern is formed on the rear focal plane FL4 of the end lens L4 which coincides with the pupil plane P.

FIG. 4B shows an example of embodiment of the present invention where the miniaturised instrument for simulating simultaneous vision by generating masks has a Mask-Generating Element EGM operating in reflection mode, an adjustable lens LA of variable focus, two end lenses L1 and L4 and two intermediate lenses L2 and L3 configured in a single optical channel CO. In the implementation shown in FIG. 4B, the incident light, which travels through the optical channel in the direction shown in FIG. 4B, consecutively traverses the adjustable lens LA, the end lens L1, the intermediate lens L2, after which it non-perpendicularly hits the mask-generating element EGM, which reflects the incident light so that it consecutively traverses the intermediate lens L3 and the end lens L4 to finally reach the pupil plane P where it projects the complete pupil pattern as described in the example of embodiment of FIG. 1A-1B. The projector lenses L1, L2, L3 and L4 have the same focal length. The separation between each two consecutive projector lenses, throughout the optical path, is equivalent to two focal lengths. The adjustable lens LA is located in the front focus FL1 of the end lens L1 and the mask-generating element EGM is located in the rear focus of the intermediate lens FL2 which coincides with the front focus FL3 of the intermediate lens L3. The complete pupil pattern P is formed on the focal plane located on the rear focus FL4 of the end lens L4.

The mask-generating element in reflection mode is what imposes an optical channel with at least one reflection. The optical channel with reflections can be used to make the system more compact. It is for this reason that the examples of embodiment shown in FIGS. 5A, 5B and 5C are more compact with respect to the examples of embodiment shown in FIG. 2, it does not alter the sight line as in FIG. 4 and the features are improved with respect to FIG. 3. The alteration of the reading distance is less in this example of embodiment, thanks to the several reflections in the optical path. Furthermore, unlike the examples of FIG. 4, the optical channel is aligned between the inlet and outlet of the instrument, so that the line of sight of the eye is not affected. In the example of embodiment of FIG. 5A, the miniaturised instrument for simulating simultaneous vision by generating masks has a Mask-Generating Element EGM, an adjustable lens LA, two end lenses L1 and L4, two intermediate lenses L2 and L3 and two mirrors E1 and E2 configured in a single optical channel CO. In the implementation shown in FIG. 5A, the incident light from the observed object (not shown in the figure), which travels through the optical channel in the direction shown in FIG. 5A, traverses the adjustable lens LA, non-perpendicularly hits the mirror E1 where it is reflected to consecutively traverse the end lens L1 and the intermediate lens L2, after which it non-perpendicularly hits the mask-generating element EGM (in reflection mode), which reflects the incident light so that it consecutively traverses the intermediate lens L3 and the end lens L4 to finally be reflected by the mirror E2 until reaching the pupil plane P where it projects the complete pupil pattern as described in the example of embodiment of FIG. 1A-1B. All the projector lenses L1, L2, L3 and L4 have the same focal length. The separation between each two consecutive projector lenses, throughout the optical path, is equivalent to two focal lengths. The mirror E1 can be found at any point of the optical channel between the adjustable lens LA and the end lens L1. The adjustable lens LA is located in the front focus FL1 of the end lens L1 and at a distance from the same equivalent to one focal length. The mask-generating element EGM is located in the rear focus FL2 of the intermediate lens L2 which coincides with the front focus FL3 of the other intermediate lens L3. The mirror E2 can be found at any point between the end lens L4 and the pupil plane P.

FIG. 5B shows an example of embodiment of the present invention more compact with respect to the examples of embodiment shown in FIGS. 2A, 2B, 4A and 4B. The miniaturised instrument for simulating simultaneous vision by generating masks has a Mask-Generating Element EGM (in transmission mode), an adjustable lens LA of variable focus, two end lenses L1 and L4, two intermediate lenses L2 and L3, two end mirrors E1 and E2 and two intermediate mirrors E3 and E4 configured in a single optical channel CO. In the implementation shown in FIG. 5B, the incident light from the observed object (not shown in the figure), which travels through the optical channel in the direction shown in FIG. 5B, traverses the mask-generating element EGM, non-perpendicularly hits the mirror E1 where it is reflected to consecutively traverse the end lens L1 and the intermediate lens L2, after which it non-perpendicularly hits the intermediate mirror E3 to traverse the adjustable lens LA and reach the other intermediate mirror E4, which reflects the incident light so that it consecutively traverses the intermediate lens L3 and the end lens L4 to finally be reflected by the mirror E2 until reaching the pupil plane P where it projects the complete pupil pattern as described in the example of embodiment of FIG. 1A-1B. All the projector lenses L1, L2, L3 and L4 have the same focal length. The separation between each two consecutive projector lenses, throughout the optical path, is equivalent to two focal lengths. The mirror E1 can be found at any point of the optical path between the end lens L1 and the mask-generating element. The mask-generating element EGM is located at a distance equivalent to one focal length from the end lens L1, throughout the optical path. The mirror E3 can be found at any point of the optical path between the intermediate lens L2 and the adjustable lens LA. In turn, the mirror E4 can be found at any point of the optical path between the adjustable lens LA and the other intermediate lens L3. The adjustable lens LA is located between both intermediate mirrors E3 and E4 at one focal length, throughout the optical path, from the intermediate lenses L2 and L3. The mirror E2 can be found at any point of the optical path between the end lens L4 and the pupil plane P where it projects the complete pupil pattern.

FIG. 5C shows an example of embodiment of the present invention more compact with respect to the examples of embodiment shown in FIGS. 2A, 2B, 3A, 3B, 3C, 4A and 4B. The miniaturised instrument for simulating simultaneous vision by generating masks has a Mask-Generating Element EGM (operating in transmission mode), an adjustable lens LA of variable focus, two end lenses L1 and L4, two intermediate lenses L2 and L3, two end mirrors E1 and E2, and two intermediate mirrors E3 and E4 configured in a single optical channel CO. In the implementation shown in FIG. 5C, the incident light from the observed object (not shown in the figure), which travels through the optical channel in the direction shown in FIG. 5C, traverses the adjustable lens LA, non-perpendicularly hits the mirror E1 where it is reflected to consecutively traverse the end lens L1 and the intermediate lens L2, after which it non-perpendicularly hits the intermediate mirror E3 to traverse the mask-generating element EGM and reach the other intermediate mirror E4, which reflects the incident light so that it consecutively traverses the intermediate lens L3 and the end lens L4 to finally be reflected by the mirror E2 until reaching the pupil plane P where it projects the complete pupil pattern as described in the example of embodiment of FIG. 1A-1B. All the projector lenses L1, L2, L3 and L4 have the same focal length. The separation between each two consecutive projector lenses, throughout the optical path, is equivalent to two focal lengths. The mirror E1 can be located at any point of the optical channel CO between the adjustable lens and the end lens L1. The adjustable lens LA is located at a distance of the end lens L1 equivalent to one focal length. The mirror E3 can be located at any point of the optical channel between the intermediate lens L2 and the mask-generating element EGM. The mirror E4 can be located at any point of the optical channel between the Mask-Generating Element EGM and the other intermediate lens L3. The mask-generating element EGM is located between both intermediate mirrors E3 and E4 at one focal length, throughout the optical path, from the intermediate lenses L2 and L3. The end lens E2 can be located at any point of the optical path between the end lens L4 and the pupil plane P where it projects the complete pupil pattern.

Figure 6A:
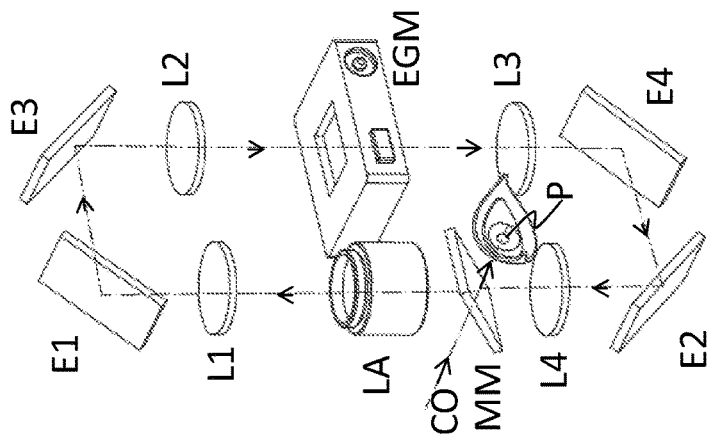
FIG. 6A shows an example of embodiment of the present invention with a Mask-Generating Element, an adjustable lens, four lenses, a double mirror and four mirrors configured in an optical channel in reflection on the mirrors and the double mirror.

FIG. 6A shows the example of embodiment of the present invention more compact than those described until now with four projector lenses. The miniaturised instrument for simulating simultaneous vision by generating masks has a Mask-Generating Element EGM, an adjustable lens LA of variable focus, a double mirror (double-sided) MM, two end lenses L1 and L4, two intermediate lenses L2 and L3, two end mirrors E1 and E2, and two intermediate mirrors E3 and E4 configured in a single optical channel CO. The inclusion of the double mirror MM at 45 degrees with respect to the incident light and also with respect to the line of sight of the eye allows that the optical channel CO undergoes a deviation which allows it to traverse the elements included in the example of embodiment shown in FIG. 6A, travelling a long optical path to return, co-aligned, to the starting point. Therefore, the reading distance is minimally affected. In the implementation shown in FIG. 6A, the incident light which travels through the optical channel CO in the direction shown in FIG. 6A, is reflected on one side of the double mirror MM, it traverses the adjustable lens LA, the end lens L1 and non-perpendicularly hits the end lens E1 where it is reflected to again be reflected by the intermediate mirror E3, after which it consecutively traverses the intermediate lens L2, the mask-generating element EGM, the intermediate lens L3 until reaching the intermediate mirror E4 where it is reflected until reaching the end lens E2, where it is again reflected to traverse the end lens L4, reaching the other side of the double mirror MM where the light is again reflected until reaching the pupil plane P where it projects the complete pupil pattern as described in the example of embodiment of FIG. 1A-1B. All the lenses have projection of the same focal length except the adjustable lens LA. All the projector lenses L1, L2, L3 and L4 have the same focal length. The separation between each two consecutive projector lenses, throughout the optical path, is equivalent to two focal lengths. The adjustable lens LA is located at one focal length from the end lens L1. The end lens E1 and the intermediate mirror E3 can be found at any point of the optical channel between the end lens L1 and the intermediate lens L2, maintaining the condition that the distance between the end lens L1 and the intermediate lens L2 throughout the optical path is of two focal lengths. The mask-generating element EGM is located equidistantly (at one focal length) from the intermediate lenses L2 and L3. The intermediate mirror E4 and the end lens E2 can be found at any point of the optical channel between the intermediate lens L3 and the end lens L4 maintaining the condition that the distance between the intermediate lens L3 and the end lens L4, throughout the optical path, is of two focal lengths. The complete pupil pattern is projected on the pupil plane P situated at one focal length from the end lens L4 throughout the optical path.

Figure 6B:
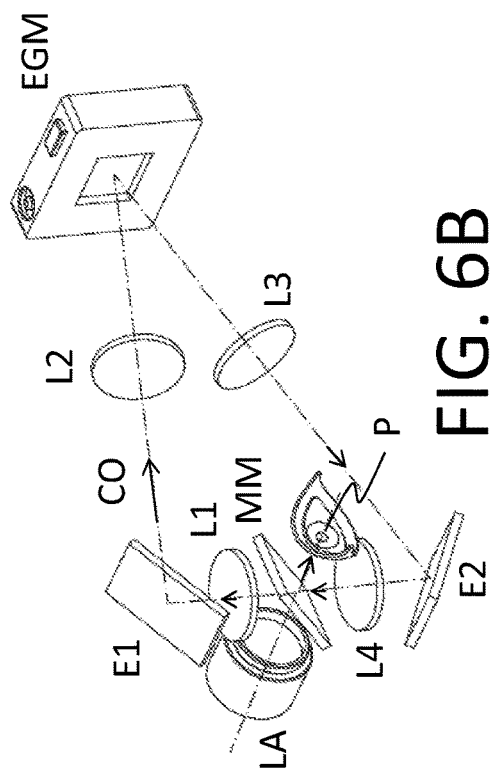
FIGS. 6B and 6C show two examples of embodiment of the present invention with a Mask-Generating Element, an adjustable lens, four lenses and two mirrors configured in an optical channel in reflection on the mirrors and the Mask-Generating Element for different combinations of the lenses, the adjustable lens, the double mirror, the mirrors and of the Mask-Generating Element.

FIG. 6B shows an example of embodiment of the present invention more compact with respect to the examples of embodiment shown in FIGS. 2A, 2B, 4A, 4B, 5A, 5B and 5C. The miniaturised instrument for simulating simultaneous vision by generating masks has a Mask-Generating Element EGM (in reflection mode), an adjustable lens LA of variable focus, a double mirror (double-sided) MM, two end lenses L1 and L4, two intermediate lenses L2 and L3, and two mirrors E1 and E2. All the previous elements are configured in a single optical channel CO. The inclusion of the double mirror MM at 45 degrees with respect to the incident light and also with respect to the line of sight of the eye allows that the optical channel CO undergoes a deviation which allows it to traverse the elements included in the example of embodiment shown in FIG. 6A, travelling a long optical path to return, co-aligned, to the starting point. Therefore, in the implementation shown in FIG. 6B, the incident light from the observed object (not shown in the figure), which travels through the optical channel in the direction shown in FIG. 6B, it traverses the adjustable lens LA, the end lens L1 and non-perpendicularly hits the end lens E1 where it is reflected to again be reflected by the intermediate mirror E3, after which it consecutively traverses the intermediate lens L2, the mask-generating element EGM, the intermediate lens L3 until reaching the intermediate mirror E4 where it is reflected until reaching the end lens E2, where it is again reflected to traverse the end lens L4, reaching the other side of the double mirror MM where the light is again reflected until reaching the pupil plane P where it projects the complete pupil pattern as described in the example of embodiment of FIG. 1A-1B. All the projector lenses L1, L2, L3 and L4 have the same focal length. The separation between each two consecutive projector lenses, throughout the optical path, is equivalent to two focal lengths. The adjustable lens LA is located in the focal plane of the end lens L1, considering the reflection in the double mirror MM, which is physically situated obliquely at approximately 45 degrees, between the adjustable lens LA and the end lens L1. In turn, by its rear side, MM is obliquely located between the end lens L4 and the pupil plane P (where the pupil of the subject's eye is located), such that the pupil plane P is in the rear focal plane of the end lens L4 because both, the end lens L4 and the pupil plane P, are at a focal of distance throughout the optical path. The mirror E1 can be found at any point of the optical channel between the end lens L1 and the intermediate lens L2. Likewise, mirror E2 can be found at any point of the optical channel between the intermediate lens L3 and the end lens L4. The mask-generating element EGM is located in the rear focus FL2 of the intermediate lens L2 which coincides with the front focus FL3 of the other intermediate lens L3. The complete pupil pattern is projected on the pupil plane P situated at one focal length from the other end lens L4.

Figure 6C:
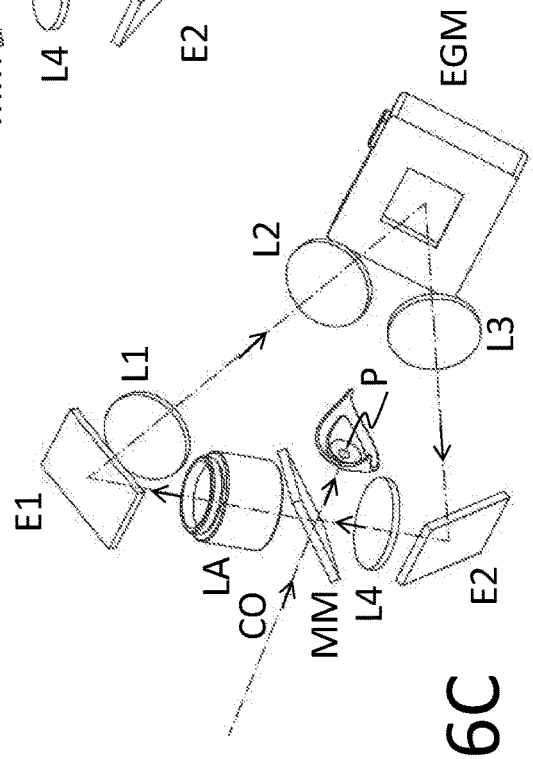

FIG. 6C shows an example of embodiment of the present invention more compact with respect to the examples of embodiment shown in FIGS. 2A, 2B, 4A, 4B, 5A, 5B and 5C. The miniaturised instrument for simulating simultaneous vision by generating masks has a Mask-Generating Element EGM, an adjustable lens LA of variable focus, a double mirror (double-sided) MM, two end lenses L1 and L4, two intermediate lenses L2 and L3, two mirrors E1 and E2, configured in a single optical channel CO. The inclusion of the double mirror MM at 45 degrees with respect to the incident light and also with respect to the line of sight of the eye allows that the optical channel CO undergoes a deviation which allows it to traverse the elements included in the example of embodiment shown in FIG. 6A, travelling a long optical path to return, co-aligned, to the starting point. Therefore, in the implementation shown in FIG. 6C, the incident light from the observed object (not shown in the figure), which travels through the optical channel in the direction shown in FIG. 6C, is reflected on one side of the double mirror MM, traverses the adjustable lens LA, is reflected in the mirror E1, consecutively traverses the end lens L1 and the intermediate lens L2 and non-perpendicularly hits the mask-generating element EGM operating in reflection mode where it is reflected to then traverse the intermediate lens L3 and be reflected by the mirror E2. The mirror E2 reflects the light and orientates it towards the end lens L4 which traverses it until reaching the other side of the double mirror MM where it is again reflected until reaching the pupil plane P (the user's pupil) where the complete pupil pattern is formed as described in the example of embodiment of FIG. 1A-1B. All the lenses have projection of the same focal length except the adjustable lens LA. All the projector lenses L1, L2, L3 and L4 have the same focal length. The separation between each two consecutive projector lenses, throughout the optical path, is equivalent to two focal lengths. The complete pupil pattern is formed on the pupil plane P situated at one focal length, throughout the optical path, from the end lens L4.

To implement the mask-generating element EGM, it is possible to use a "Digital Micromirror Device" (DMD) or a "Spatial Light Modulator" (SLM) for any previous embodiments. The "Spatial Light Modulator" can function in reflection mode or in transmission mode. However, the "Digital Micromirror Device" (DMD) only operates in reflection.

The invention claimed is:

1. A miniaturised instrument for simulating simultaneous vision by generating masks, characterised in that it comprises:
a mask-generating element which generates at least two complementary masks, with a temporal frequency of alternation such that, sequentially, each mask lets an incident light from an object partially pass, at the same time as the at least one other mask partially blocks said incident light;
an adjustable lens of variable optical power which generates, with said temporal frequency of alternation, at least two different optical powers corresponding to at least two observation distances;
wherein the mask-generating element and the adjustable lens are located in a single optical channel wherethrough said incident light circulates, such that each mask of the mask-generating element is temporally synchronised with each power of the adjustable lens, obtaining, via temporal fusion, a combined pupil pattern of at least two observation distances.

2. The miniaturised instrument for simulating simultaneous vision by generating masks according to claim 1, wherein the frequency of alternation is preferably greater than 30 Hz, and more preferably greater than 60 Hz.

3. The miniaturised instrument for simulating simultaneous vision by generating masks according to claim 1, wherein it additionally comprises two projector lenses, both with the same focal length and separated from one another by two focal lengths; such that the mask-generating element is located in the front focus of one of the lenses, and the adjustable lens is approximately placed in the rear focus of the other lens, forming the pupil pattern on the rear focus of said other lens.

4. The miniaturised instrument for simulating simultaneous vision by generating masks according to claim 1, wherein it additionally comprises two projector lenses with the same focal length and separated from one another by two focal lengths; such that the adjustable lens is located in the front focus of one of the lenses and the mask-generating element is approximately placed in the rear focus of the other lens, forming the pupil pattern on the rear focus of said other lens.

5. The miniaturised instrument for simulating simultaneous vision by generating masks according to claim 1, wherein it additionally comprises two projector lenses with the same focal length and separated from one another by two focal lengths; such that the adjustable lens and the mask-generating element is located in the front focus of one of the lenses, and the pupil pattern is formed on the rear focal plane of said other lens.

6. The miniaturised instrument for simulating simultaneous vision by generating masks according to claim 1, additionally comprising four projector lenses, two end and two intermediate, with the same focal length, consecutively distributed on said optical channel and with a separation between each two consecutive lenses equivalent to two focal lengths, such that the mask-generating element is located in the front focus of one of the end lenses, the adjustable lens LA is located in the rear focus of one of the intermediate lenses which coincides with the front focus of the other intermediate lens, and the pupil pattern is formed on the rear focus of the other end lens.

7. The miniaturised instrument for simulating simultaneous vision by generating masks according to claim 1, additionally comprising four projector lenses, two end and two intermediate, with the same focal length, consecutively distributed on said optical channel and with a separation between each two consecutive lenses equivalent to two focal lengths, such that the adjustable lens is located in the front focus of one of the end lenses, the mask-generating element is located in the rear focus of one of the intermediate lenses which coincides with the front focus of the other intermediate lens, and the pupil pattern is formed on the rear focus of the other end lens.

8. The miniaturised instrument for simulating simultaneous vision by generating masks according to claim 6, wherein the mask-generating element is located non-perpendicularly to the optical channel, such that the mask-generating element, operating in reflection mode, directly receives the incident light and reflects it in another direction, wherein it traverses the four projector lenses and the adjustable lens.

9. The miniaturised instrument for simulating simultaneous vision by generating masks according to claim 7, wherein the mask-generating element is located non-perpendicularly to the optical channel, such that the mask-generating element, operating in reflection mode, receives the incident light through the adjustable lens, of an end lens and an intermediate lens, and reflects it in another direction, wherein it traverses an intermediate lens and an end lens.

10. The miniaturised instrument for simulating simultaneous vision by generating masks according to claim 1, additionally comprising: four projector lenses, two end and two intermediate, with the same focal length, consecutively distributed on said optical channel and with a separation between each two consecutive projector lenses equivalent to two focal lengths; and two end mirrors; where the instrument is configured such that the incident light runs consecutively through: the adjustable lens, an end mirror, an end lens, an intermediate lens, the mask-generating element in reflection mode, the other intermediate lens, the other end lens and the other mirror, until reaching the pupil plane.

11. The miniaturised instrument for simulating simultaneous vision by generating masks according to claim 1, additionally comprising: four projector lenses, two end and two intermediate, with the same focal length, consecutively distributed on said optical channel and with a separation between each two consecutive projector lenses equivalent to two focal lengths; two end mirrors and two intermediate mirrors; where the instrument is configured such that the incident light runs consecutively through: the mask-generating element, an end mirror, an end lens, an intermediate lens, an intermediate mirror, the adjustable lens, the other intermediate mirror, the other intermediate lens, the other end lens and the other end mirror until reaching the pupil plane.

12. The miniaturised instrument for simulating simultaneous vision by generating masks according to claim 1, additionally comprising: four projector lenses, two end and two intermediate, with the same focal length, consecutively distributed on said optical channel and with a separation between each two consecutive projector lenses equivalent to two focal lengths; two end mirrors and two intermediate mirrors; where the instrument is configured such that the incident light runs consecutively through: the adjustable lens, an end mirror, an end lens, an intermediate lens, an intermediate mirror, the mask-generating element, the other intermediate mirror, the other intermediate lens, the other end lens and the other end mirror until reaching the pupil plane.

13. The miniaturised instrument for simulating simultaneous vision by generating masks according to claim 1, additionally comprising: four projector lenses, two end and two intermediate, with the same focal length; two end mirrors and two intermediate mirrors; and, a double mirror; where the instrument is configured such that the incident light consecutively runs through one side of the double mirror, the adjustable lens, an end lens, an end mirror, an intermediate mirror, an intermediate lens, the mask-generating element, the other intermediate lens, the other intermediate mirror, the other end mirror, the other end lens and the other side of the double mirror until reaching the pupil plane.

14. The miniaturised instrument for simulating simultaneous vision by generating masks according to claim 1, additionally comprising: four projector lenses, two end and two intermediate, with the same focal length; two end mirrors; and a double mirror; where the instrument is configured such that the incident light consecutively runs through one side of the double mirror, the adjustable lens, an end mirror, an end lens, an intermediate lens, the mask-generating element, the other intermediate lens, the other end mirror, the other end lens and the other side of the double mirror (MM) until reaching the pupil plane (P).

15. The miniaturised instrument for simulating simultaneous vision by generating masks according to claim 1, additionally comprising: four projector lenses, two end and two intermediate, with the same focal length; two end mirrors; and a double mirror; where the instrument is configured such that the incident light consecutively runs through the adjustable lens, one side of the double mirror, an end lens, an end mirror, an intermediate lens, the mask-generating element, the other intermediate lens, the other end mirror, the other end lens and the other side of the double mirror, until reaching the pupil plane.

16. A use of the instrument according to claim 1, in combination with glasses, contact lenses, intraocular lenses, refractive surgery or other ophthalmic or surgical corrections.

17. A use of the instrument according to claim 1, as phoropter.

18. A use of the instrument according to claim 1, in combination with visual or psychophysical tests.

19. A use of the instrument according to claim 1, to assess the tolerance of patients to simultaneous vision corrections or for the training of the patient prior to the implantation of simultaneous vision corrections.

20. A use of the instrument according to claim 1, to determine or select the parameters of a simultaneous vision correction at the time of the design thereof or during the prescription or selection of the most suitable correction for a certain patient or for a group of patients.

* * * * *